United States Patent [19]
Nakamura

[11] Patent Number: 5,225,958
[45] Date of Patent: Jul. 6, 1993

[54] ELECTRONIC ENDOSCOPE APPARATUS CAPABLE OF PROTECTING OVERVOLTAGE FOR SOLID-STATE IMAGE SENSOR

[75] Inventor: Toru Nakamura, Tochigi, Japan

[73] Assignee: Kabushiki Kaisha Toshiba, Kawasaki, Japan

[21] Appl. No.: 773,528

[22] Filed: Oct. 9, 1991

[30] Foreign Application Priority Data

Oct. 9, 1990 [JP] Japan .................................. 2-271719

[51] Int. Cl.$^5$ .............................................. H02H 3/22
[52] U.S. Cl. ........................................ 361/55; 361/56; 361/91; 361/111; 128/901; 358/98
[58] Field of Search ............... 361/55, 56, 58, 91, 361/111; 128/901, 908, 4; 358/98, 463

[56] References Cited

U.S. PATENT DOCUMENTS

4,587,588  5/1986  Goldstein ............................. 361/55
5,146,384  9/1992  Markovic et al. ..................... 361/55
5,159,518 10/1992  Roy ...................................... 361/56

Primary Examiner—Todd E. DeBoer
Attorney, Agent, or Firm—Foley & Lardner

[57] ABSTRACT

In an electronic endoscope apparatus, an overvoltage is produced by discharging electrostatic energy induced on an electronic scope made of a synthetic resin. The electronic scope used for the electronic endoscope apparatus comprises: a solid-state image sensor for producing an image signal of a biological body under medical examination, the image signal being derived from a signal line of the image sensor; and, an overvoltage protecting circuit for protecting the image sensor against an overvoltage caused by at least one of electrostatic energy induced on the electronic scope and interruption of source power supplied from the electronic endoscope apparatus to the image sensor, by maintaining at least said signal line at the same potential.

16 Claims, 10 Drawing Sheets

ELECTRONIC ENDOSCOPE APPARATUS CAPABLE OF PROTECTING OVERVOLTAGE FOR SOLID-STATE IMAGE SENSOR

BACKGROUND OF THE INVENTION

1. Field of the Invention

The present invention generally relates to an electronic endoscope apparatus including an electronic scope with a solid-state image sensor. More specifically, the present invention is directed to an overvoltage protection means for such a solid-state image sensor employed in the electronic scope of the electronic endoscope apparatus.

2. Description of the Prior Art

Figure 1:
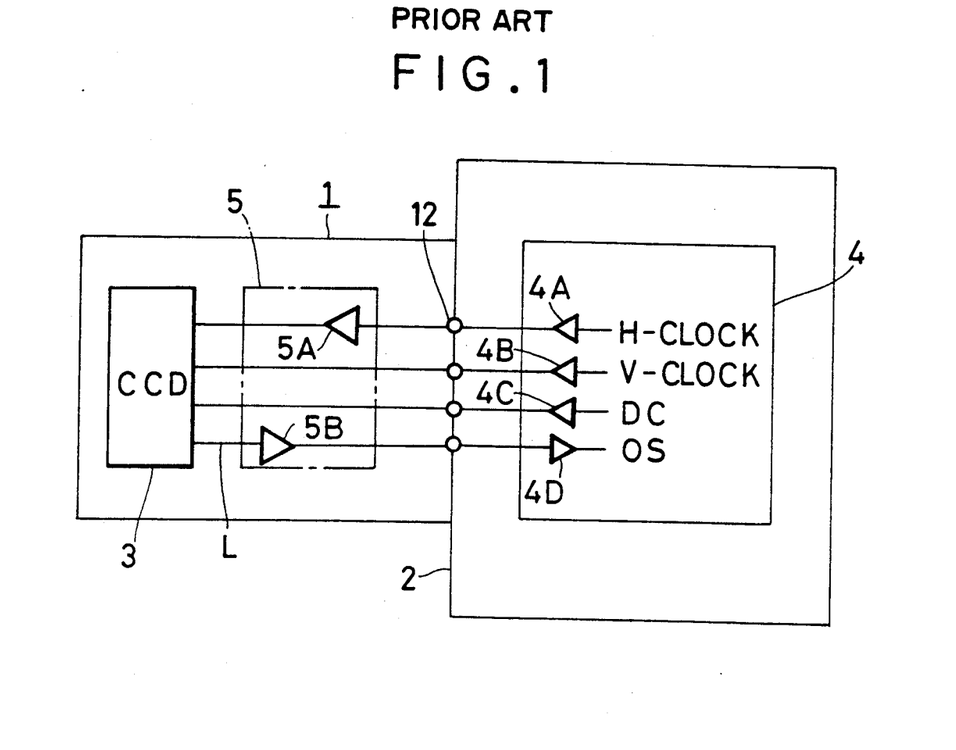
FIGS. 1 and 2 schematically illustrate the conventional electronic endoscope apparatus equipped with the electronic scope having CCD.

A solid-state image sensor such as a change-coupled device (CCD) has been widely utilized in the electronic endoscope apparatuses. As shown in FIG. 1, such a solid-state image sensor is mounted at a tip (distal end) portion of an electronic scope 1, that will converts an optical signal of an image of an object (not shown in detail) under medical examination, into a corresponding electronic signal of this potential image. In general, a length of the electric scope 1 is amount to approximately 1 meter to 5 meters, and a material of the electronic scope 1 is made of a synthetic resin, which may readily induce static electric (electrostatic) energy. Accordingly, there are many possibilities that the static electric energy can sufficiently give serious damages to the solid-state image sensor, e.g., statically break down this image sensor.

Also, the electronic scope 1 has a connector 12 at the other end thereof. The function of this connector 12 is to disconnect the dirty electronic scope 1 from a main body of the electronic endoscope apparatus 2 for cleaning purposes.

As is known, in the main body of the electronic endoscope apparatus 2, the drive signal for CCD 3 is produced and supplied via the connector 12 of the electronic scope 1 to CCD 3, and furthermore, am image processor 4 is employed to process the electric image signal derived from CCD 3, thereby displaying endoscopic images of the biological body under medical examination on a TV monitor (not shown in detail). This processor 4 further employs digital drivers 4A, 4B, 5A and buffer amplifiers 4C, 4D, 5B for amplifying these signals.

More specifically, the drive signals for CCD 3 are the horizontal transfer clock "H-CLOCK" having a high frequency (e.g., 5 to 9 V at 14 MHz), the vertical transfer clock "V-CLOCK" having a low frequency (e.g., 3-value digital signal with −9 V, O V and 15 V), and DC voltages (e.g., overflow drain voltages). Furthermore, a very small picture signal "OS" is outputted from CCD 3, the frequency of which is the same as that of the horizontal transfer clock "H-CLOCK".

As previously explained, since both the horizontal transfer clock "H-CLOCK" and the picture signal "OS" are of the high frequency signal and furthermore the electronic scope 1 employs such long signal lines "L", the signal levels of these RF signals are lowered due to the transmission loss, resulting in deterioration of endoscopic images. Accordingly, some of the conventional electronic endoscope apparatus additionally employ a repeating circuit 5 so as to compensate for the transmission loss of the high frequency signals.

In the above-described conventional electronic endoscope apparatus with such a solid-state image sensor, there are the following problems.

First, since the electronic scope 1 made of the synthetic resin must be frequently cleaned with a cotton gauze during diagnostic operations, electrostatic energy is easy to be induced on this resin scope 1.

Secondly, since electric insulation of the electronic scope 1 is absolutely necessary for preventing averse influences to a human body (this scope is actually and directly inserted into a body cavity of a human body), such an electrostatic energy may be further induced.

Thirdly, since an electronic endoscope apparatus is operable in conjunction with an electrocautery while electrically connecting an electronic scope therewith, electromagnetic leaks may occur in the conducting wire of the electric scope, so that the electric insulating material must be used to manufacture the electronic scope, which may readily induce electrostatic energy thereon.

Figure 2:
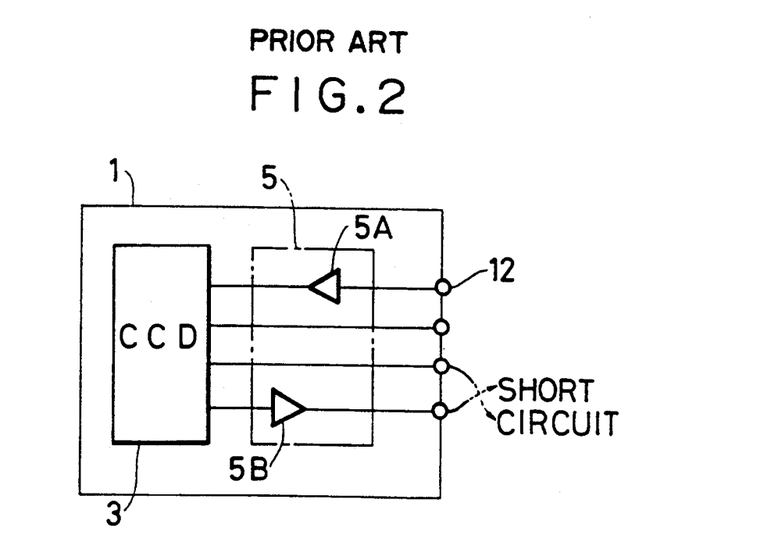

Furthermore, when the electronic scope 1 is disconnected from the main body of the electronic endoscope apparatus 2, metal pins of the connector 12 are exposed, as represented in FIG. 2, and may be shortcircuited by another metal portion of the main body, e.g., a metal frame connected to ground. Otherwise, discharge energy caused by shortcircuiting the electrostatic energy via these connector pins may give electrical damage to CCD 3 or the repeating circuit 5.

Also, there is another problem that if such an erroneous operation happens to occur that the electronic scope 1 is connected/disconnected with the main body 2 while electric power is supplied from the main body to the electric scope 1, either CCD 3 or the repeater circuit 5 is electrically destroyed.

The present invention has been made in an attempt to solve the above-described various problems, and therefore has an object to provide an electronic endoscope apparatus equipped with an electronic scope having a solid-state image sensor, capable of preventing electric destruction of a solid-state image sensor caused by overvoltages induced on the electronic scope 1.

SUMMARY OF THE INVENTION

To achieve the above-explained object and other features, an electronic endoscope apparatus, according to the present invention, comprises:

a solid-state image sensor (3) for producing an image signal of a biological body under medical examination, said image signal being derived from a signal line (L) of the image sensor (3); and, overvoltage protecting means (20:600) for protecting said image sensor (3) against an overvoltage caused by at least one of electrostatic energy induced on the electronic scope (10A: 10H) and interruption of source power supplied from the electronic endoscope apparatus (2) to the image sensor (3), by maintaining at least said signal line (L) at the same potential.

BRIEF DESCRIPTION OF THE DRAWINGS

For a better understanding of the present invention, reference is made of the following detailed description in conjunction with the accompanying drawings, in which.

DETAILED DESCRIPTION OF THE PREFERRED EMBODIMENTS

Basic Idea

Figures 3, 4:
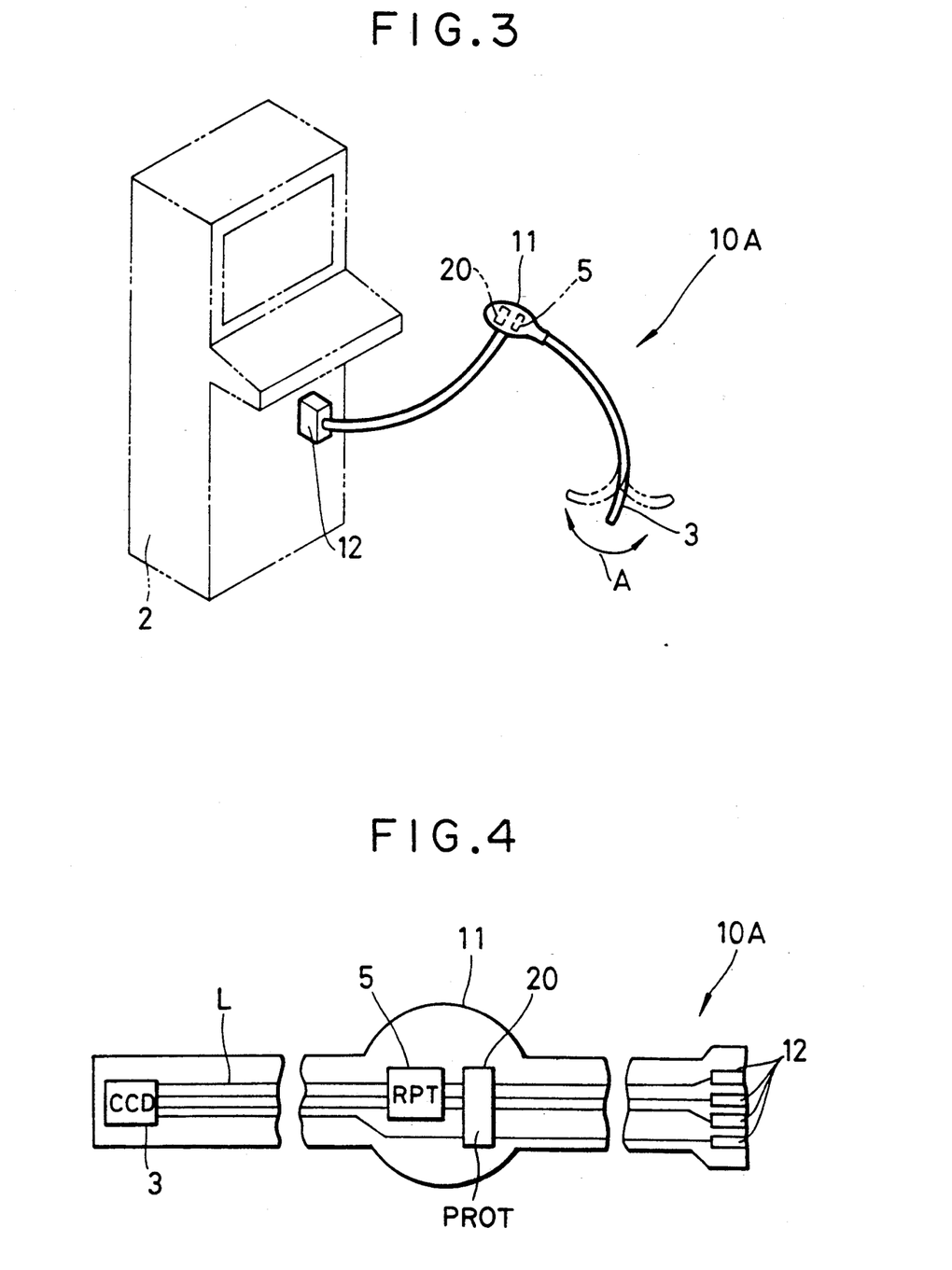
FIGS. 3 and 4 schematically represent a basic idea of an electronic endoscope apparatus equipped with an electronic scope having a solid-state image sensor, according to the present invention.

Referring now to FIGS. 3 and 4, a basic idea of the present invention will be described.

FIG. 3 schematically illustrates an electronic scope 10A connected to the main body of the electronic endoscope apparatus 2 and FIG. 4 schematically represents an internal arrangement of the electronic scope 10A comprising an overvoltage protector 20 into which the basic idea of the present invention has been applied.

The electronic scope 10A is detachably connected to the main body of the electronic endoscope apparatus 2 as shown in FIG. 3. The electronic scope 10A comprises a CCD 3 functioning as a solid-state image sensor mounted at a tip portion thereof; an operation unit 11 formed in an intermediate portion thereof along a longitudinal direction of this scope 2; a repeater circuit 5 for repeating or amplifying RF signals derived from CCD 3; and a connector 12 for electrically connecting this electronic scope 10A to the main body of the electronic endoscope apparatus 2. The electronic scope 10A further comprises an overvoltage protecting circuit 20 interposed between the repeater circuit 5 and the connector 12. This overvoltage protecting circuit 20 constitutes a major feature of the present invention, and can set the respective circuit portions of the electronic scope 10A to the same potential, e.g., a ground potential, even when electrostatic energy induced on the electronic scope 10A happens to be discharged and therefore an overvoltage appears.

Although not shown in these drawings, the electronic scope 10A further comprises a mechanism capable of bending the tip portion along an arrow direction "A"; operation switches for controlling operations of the endoscope apparatus 2, and a signal recording circuit having no relationship with operations of CCD 3.

As previously described, the overvoltage protecting circuit 20 constructed according to the basic idea of the present invention, has such particular advantages that an application of the overvoltage to the solid-state image sensor 3, repeater circuit 5 and other electronic circuits can be prevented, or electronic damages caused by the overvoltage can be protected for these internal circuits under such these conditions: the electronic scope 10A is electrically connected with the main body of the electronic endoscope apparatus 2; the scope 10A is disconnected therefrom; and the scope 10A is transiently connected or disconnected therefrom.

First Overvoltage Protector

Figure 5:
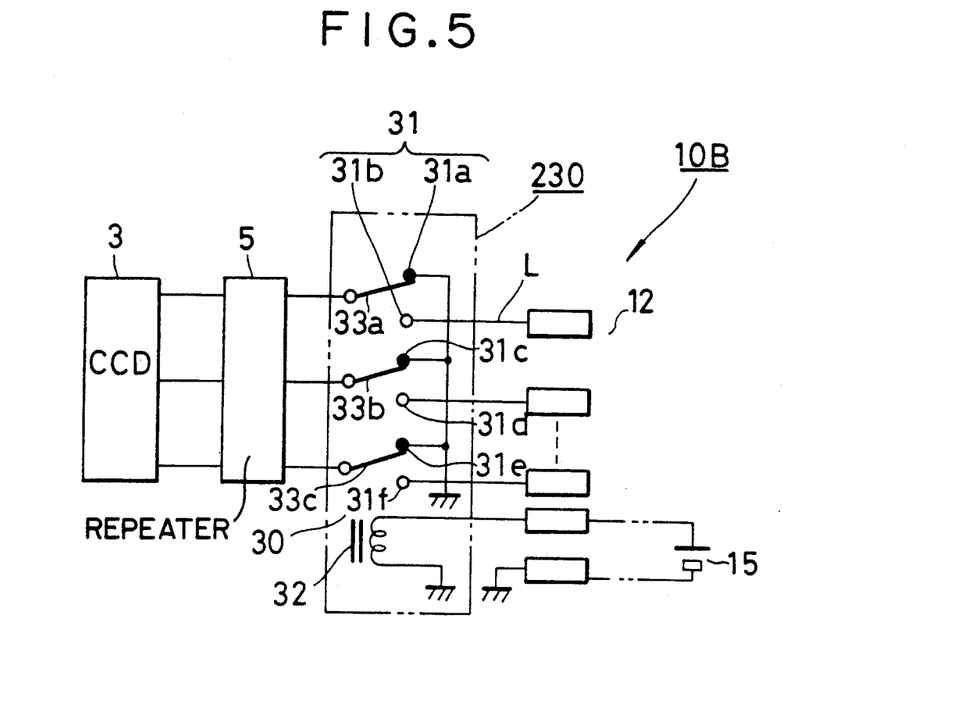
FIG. 5 is a schematic diagram of an electronic scope 10B having an overvoltage protector 230 according to a first preferred embodiment of the present invention.

FIG. 5 schematically shows an arrangement of an overvoltage protecting circuit 230 employed in an electronic scope 10B according to a first preferred embodiment of the present invention, in which the above-described basic idea of the present invention is realized.

It should be noted that the digital drivers 4A, 4B, 5A and the operational amplifiers 4C, 4D and 5B have been omitted in FIG. 5 and also the subsequent drawings, which should also be protected against such overvoltages.

The first overvoltage protecting circuit 230 is constructed of a relay 30. This overvoltage protecting circuit 30, repeater circuit 5, CCD 3 and connector 12 constitute the first electronic scope 10B.

The relay 30 of the first overvoltage protecting circuit 230 is constructed of a plurality of relay contacts 31 (31a to 31f), three contact blades 33a to 33c, and a single relay coil 32. The relay coil 32 is energized by a DC power source 15 via the connector 12.

The first overvoltage protecting circuit 230 is so designed that while the connector 12 of the first electronic scope 10B is connected to the main body of the electronic endoscope apparatus 2 (see FIG. 3), since the relay coil 32 is energized, the respective contact blades 33a to 33c are changed from the relay contacts 33a, 33c, and 33e into the relay contacts 33b, 33d and 33f. Accordingly, CCD 3 is electrically connected via the repeater circuit 5, first overvoltage protecting circuit 230 and connector 12 to the related circuit (not shown) employed in the main body of the electronic endoscope apparatus 2. To the contrary, when this connector 12 is disconnected from the main body of the electronic endoscope apparatus 2, the relay coil 32 is no longer energized by the DC power source 15, the relay contact blades 33a to 33c are connected to the relay contacts 31a, 31c and 31e which are grounded, so that all of the conducting (signal) lines of CCD 3 are maintained at the same potential, or ground potential.

As a consequence, even when the connector 12 is electrically in contact with an external circuit (not shown in detail) having a certain potential while this connector 12 is disconnected from the main body of the electronic endoscope apparatus 2, both CCD 3 and repeater circuit 5 and the like never receive any potential or electrostatic energy, because all of the signal lines are grounded via the relay 30 of the first overvoltage protecting circuit 230.

Second Overvoltage Protector

Figure 6:
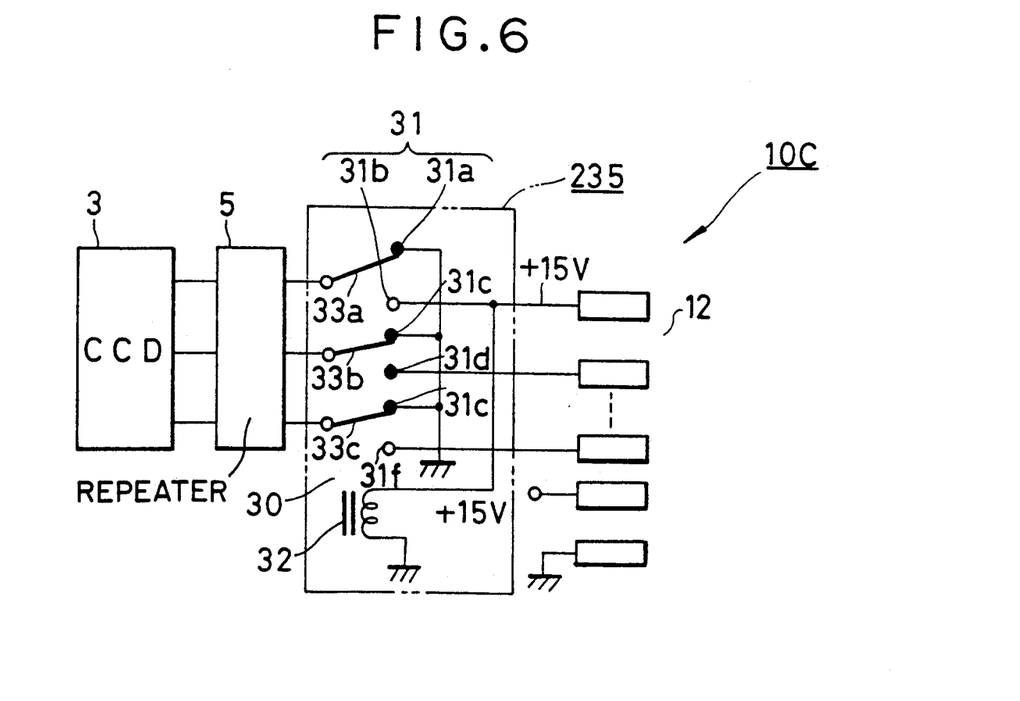
FIG. 6 schematically shows an overvoltage protector 235 employed in an electronic scope 10C according to a second preferred embodiment of the present invention.

FIG. 6 schematically shows an arrangement of an overvoltage protecting circuit 235 employed in an electronic scope 10C according to a second preferred embodiment of the present invention.

As apparent from this circuit arrangement of FIG. 6, the major circuit of the second overvoltage protecting circuit 235 is very similar to that of the first overvoltage protecting circuit 230 shown in FIG. 5. An only different or featured circuit of the second overvoltage protecting circuit 235 is the connection method of the relay coil 32. That is to say, this relay coil 32 is energized by receiving the DC supply voltage (e.g., +15 V) for driving CCD 3. Since both the overvoltage protection by the second overvoltage protecting circuit 235 and the operation of the relay 30 are the same as those of the first overvoltage protecting circuit 230, no further detail description thereof is made in the specification.

Third Overvoltage Protector

Figure 7:
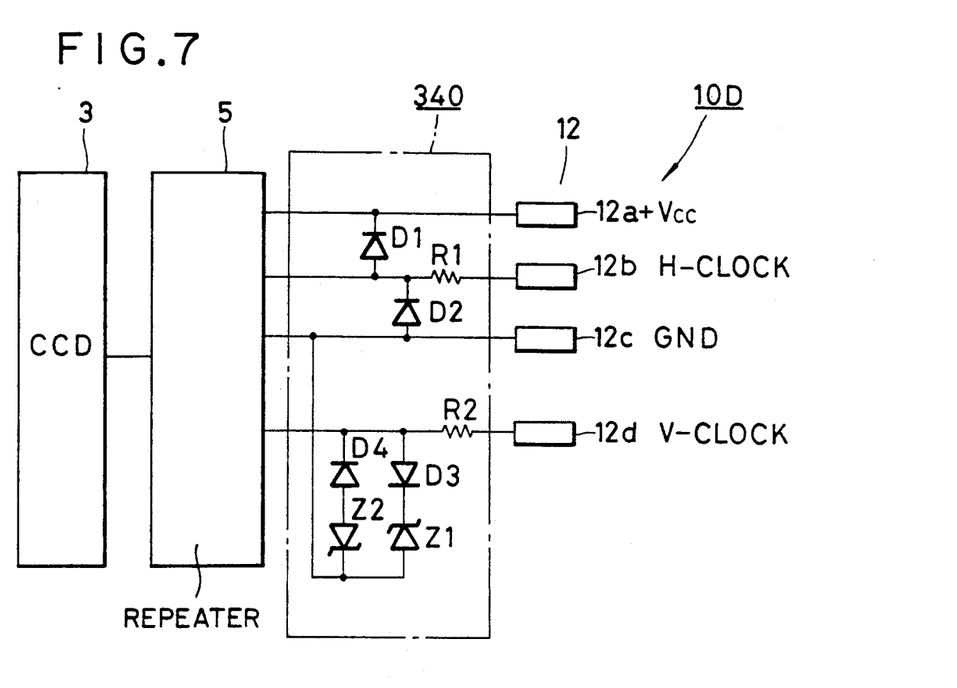
FIGS. 7, 8A and 8B represent an overvoltage protector 340 employed in an electronic scope 10D, and also operations thereof, according to a third preferred embodiment of the present invention.
Figure 8A:
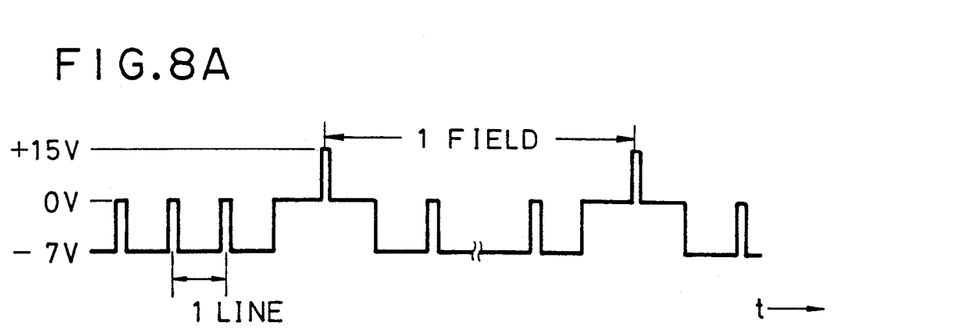
Figure 8B:
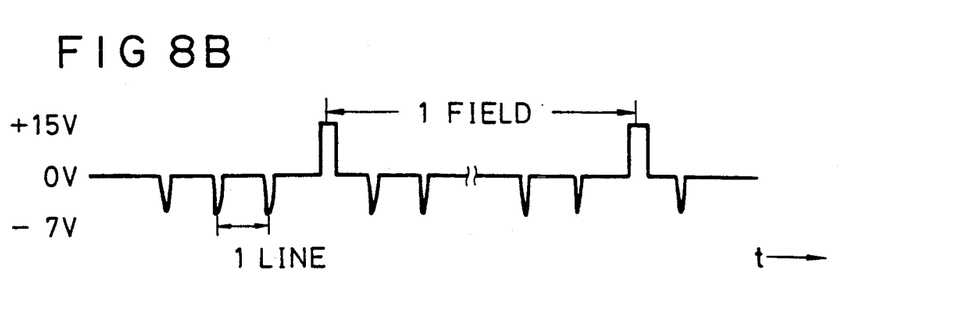

Referring now to FIGS. 7, 8A and 8B, an overvoltage protecting circuit 340 employed in an electronic scope 10D according to a third preferred embodiment of the present invention, will be described.

The third overvoltage protecting circuit 340 is so arranged by diodes D1 and D2 which are connected between a power supply connector pin 12a of the connector 12 and a horizontal clock (and also picture signal) pin 12b thereof, and also between this horizontal clock pin 12b and a ground connector pin 12c thereof. A resistor R1 is inserted into the signal line of this horizontal clock pin 12b. The third overvoltage protecting circuit 340 further comprises diodes D3, D4 and zener diodes Z1, Z2 connected between a vertical clock connector pin 12d of the connector 12 and the above-described ground connector pin 12c thereof. Another resistor R2 is inserted into the signal line of the vertical clock pin 12d.

As is known in this technical field, a 3-level signal as shown in FIGS. 8A or 8B is supplied to CCD 3 as the vertical clock via the vertical clock connector pin 12d and the ground connector pin 12c.

According to the third overvoltage protecting circuit 340, the overvoltage protecting effect thereof can be especially achieved when such a 3-level signal is received.

Precisely speaking, even when these connector pins 12a to 12d are externally in contact with each other under such a condition that the third electronic scope 10D is disconnected from the main body of the electronic endoscope apparatus 2, a lower voltage that never electrically destroys or never gives damage to CCD 3 and repeater circuit 5, is merely applied to CCd 3 and repeater circuit 5, namely a potential difference among these diodes D1 to D4. Furthermore, it is prevented by employing the diodes D1 and D2 that currents flow from the power supply connector pin 12a and horizontal clock connector pin 12b to the ground connector pin 12c. Similarly, it is prevented by employing the zener diodes Z1, Z2 that another current flows from the vertical clock connector pin 12d to the ground connector pin 12c.

Also, in accordance with the third overvoltage protecting circuit 340, there are particular two advantages: Damages caused by the electrostatic discharge phenomenon can be prevented, but also overvoltages applied from the power supply (not shown in detail) employed in the main body of the electronic endoscope apparatus 2 can be protected with respect to CCD 3 and repeater circuit 5, which may occur in such a condition. That is, while the third electronic scope 10D is connected to the main body and the power is supplied from the main body to the CCD 3, this scope 10D may be mistakenly disconnected from the main body.

This particular advantage will now be summarized. For instance, even when a positive overvoltage is applied to the horizontal clock connector pin 12b, the current merely flows through the resistor R1 and diode D1 to the power supply connector pin 12a, whereby no overvoltage is applied to the repeater circuit 5 and CCD 3. also, even if a negative overvoltage is applied to the ground connector pin 12c, the current merely flows through the diode D2 and resistor R1 into the horizontal clock connector pin 12b, so that such an overvoltage will never be applied to destroy CCD 3 and repeater circuit 5.

Fourth Overvoltage Protector

Figure 9:
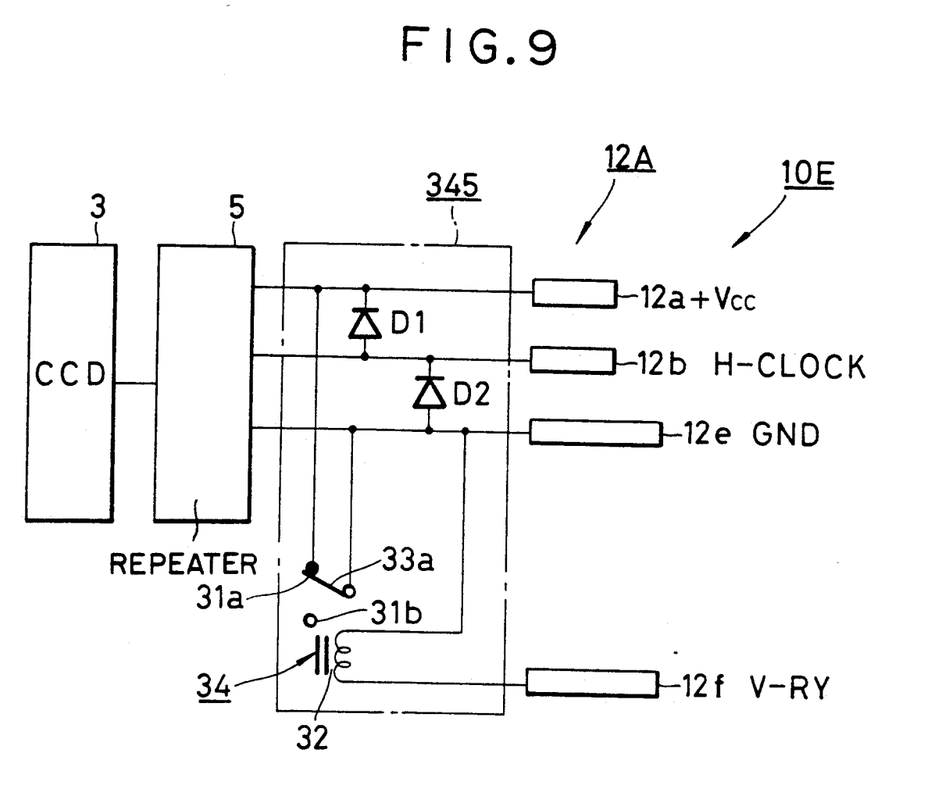
FIGS. 9 and 10 represent an overvoltage protector 345 employed in an electronic scope 10E and operations thereof, according to a fourth preferred embodiment of the present invention.

FIG. 9 schematically illustrates an arrangement of another overvoltage protecting circuit 345 and a connector 12A employed in an electronic scope 10E according to a fourth preferred embodiment of the present invention.

As apparent from FIG. 9, both the fourth overvoltage protecting circuit 345 and the connector 12A constitute a major featured construction of the forth preferred embodiment.

The fourth overvoltage protecting circuit 345 includes two diodes D1 and D2, and also a relay 34 having a single contact/blade structure. The connector 12A is constructed of two sets of short-length connector pins 12a, 12b and two sets of long-length connector pins 12e, 12f.

Figure 10:
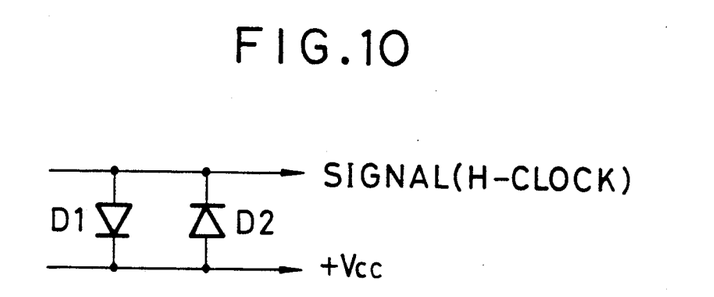

With the above-described scope construction, when the electronic scope 12E is disconnected from the main body of the electronic endoscope apparatus 2, this relay 34 is energized so that the contact blade 33a is in contact with the first contact 31a. That is, the power supply connector pin 12a is connected or shortcircuited via the first contact 31a and contact blade 33a to the ground connector pin 12e. This connection or shortcircuit condition is shown in FIG. 10 as an equivalent circuit. Accordingly, since only a voltage difference caused by a single diode D1 or D2 is applied to the repeater circuit 5 and CCD 3, even if the electronic scope 10D is connected/disconnected from the main body of the electronic endoscope apparatus 2 while power is supplied from the main body to the respective circuits, both CCD 3 and repeater circuit 5, and also other circuits are not electrically damaged or destroyed.

Fifth Overvoltage Protector

Figures 11, 12:
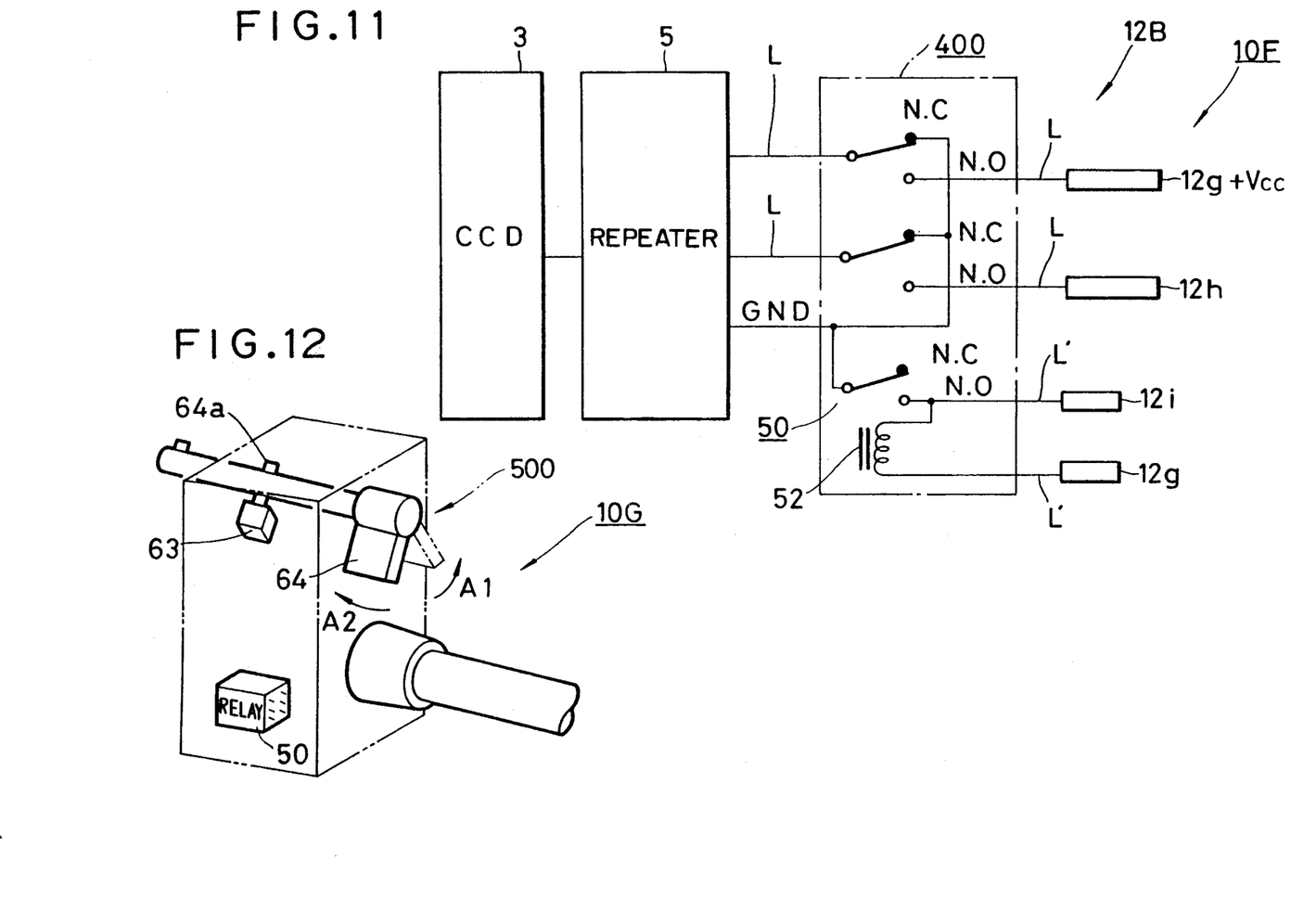
FIG. 11 schematically represents an overvoltage protector 400 employed in an electronic scope 10F according to a fifth preferred embodiment of the present invention.
FIG. 12 is an illustration of an overvoltage protector 500 employed in an electronic scope 10G according to a sixth preferred embodiment of the present invention.

FIG. 11 mainly shows an overvoltage protecting circuit 400 and a connector 10F employed in an electronic scope 10F according to a fifth preferred embodiment of the present invention.

The fifth overvoltage protecting circuit 400 is constructed of a normal-close type relay 50 having three sets of contacts and a relay coil 52. The connector 12B includes two sets of long-length connector pins 12g, 12h, for the repeater circuit 5 and CCD 3, and also two sets of short-length connector pins 12i, 12j for the relay coil 52. This relay 50 electrically connects and disconnects the signal line "L" and a power source line for the relay 50 "L".

In accordance with the fifth preferred embodiment, when the connector 12B is tried to be connected to the main body of the electronic endoscope apparatus 2, the connection with the signal line "L" is first established and thereafter the power source line "L" for the normal-close type relay 50 is connected with the main body, whereby the relay 50 can be turned ON after all of the long-length connector pins 12g, 12h have been completely connected to the main body. In other words, after the normal-close type relay 50 has been completely turned ON, the source voltage Vcc can be applied via the relay 50 or fifth overvoltage protecting circuit 400 to the internal circuits 3, 5 employed in this electronic scope 10F.

Conversely, when the connector 12B is tried to be disconnected from the main body of the electronic endoscope apparatus 2, the short-length connector pins 12i, 12j are disconnected therefrom at first so that this relay 52 is turned OFF. As a result, CCD 3 and repeater circuit 5 are grounded via the relay contacts, or maintained at the same potential.

In accordance with this fifth preferred embodiment, since the respective circuit lines of CCD 3 and repeater circuit 5 can be surely brought into the same potential, e.g., ground potential. When the fifth electronic scope 10F is connected/disconnected to/from the main body of the electronic endoscope apparatus 2, no extra load is loaded on these repeater circuit 5 and CCD 3 and also damages of these circuits caused by overvoltages can be prevented by the fifth overvoltage protecting circuit 400.

Sixth Overvoltage Protector

FIG. 12 schematically illustrates an electronic scope 10G according to a sixth preferred embodiment of the present invention.

This sixth electronic scope 10G mainly includes the above-described relay 50 and a mechanism for driving this relay 50. That is, a sixth overvoltage protector 500 employs the relay 50, a switch 63 for turning ON/OFF the power supply to the relay coil 52, and a projection 64a formed on a lever 64, which constitute the above mechanism.

In the sixth overvoltage protector 500, when the lever 64 is pivoted along an arrow direction "A1", the projection 64a formed on this lever 64 may depress the switch 63 so that the relay coil 52 is disenergized (turned OFF) and therefore the respective lines of CCD 3 and repeater circuit 5 are maintained at the same potential (ground potential) via the relay contacts. When the lever 64 is pivoted along another arrow direction "A2" opposite to the arrow direction "A1", the relay 50 is turned ON whereby both CCD 3 and repeater circuit 5 are brought into active states.

As a consequence, since the respective signal/power source lines of CCD 3, repeater circuit 5 and other circuits are maintained at the same potential, e.g., ground potential by pivoting the lever 64, electric damages of these electronic circuits employed in the firth electronic scope 10F, which are caused by discharging electrostatic energy, can be prevented.

Seventh Overvoltage Protector

Figure 13:
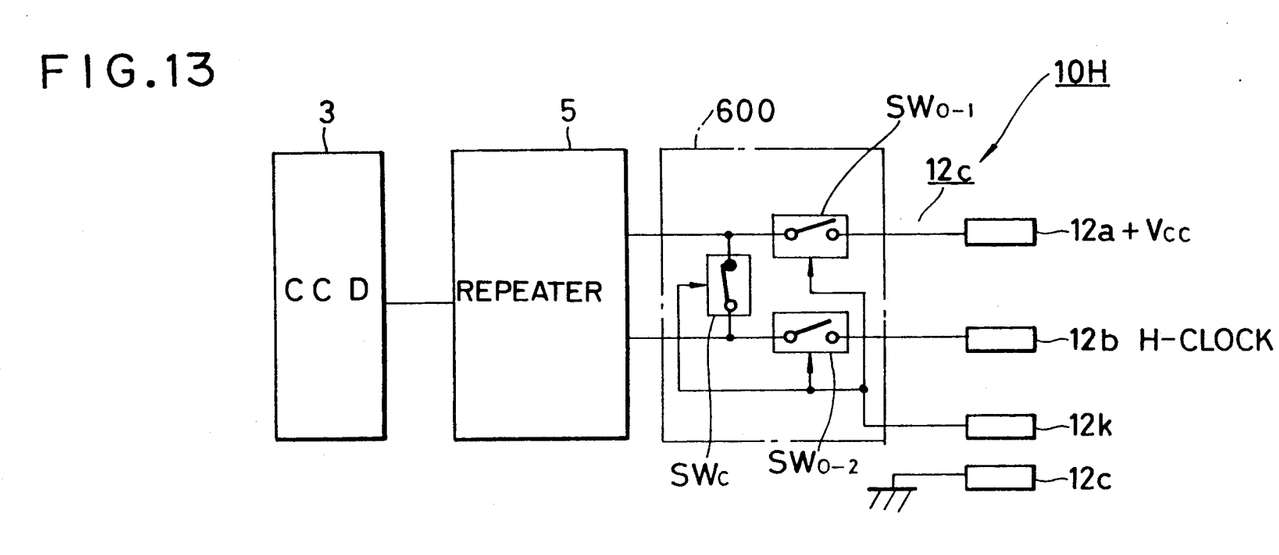
FIGS. 13, 14A and 14B represent an overvoltage protector 600 employed in an electronic scope 10H and modifications thereof, according to a seventh preferred embodiment of the present invention; and, FIGS. 15A to 15C and 16 represent modifications of the overvoltage protector according to the present invention.

FIG. 13 is a schematic illustration of an arrangement of an overvoltage protecting circuit 600 and a connector 12C employed in an electronic scope 10H according to a seventh preferred embodiment of the present invention.

The seventh overvoltage protecting circuit 600 includes two sets of normal-open type semiconductor switches $SW_{0-1}$ and $SW_{0-2}$, and one normal-close type semiconductor switch SWc. Gate electrodes of these semiconductor switches SWc, $SW_{0-1}$, $SW_{0-2}$ are connected via a gate control connector pin 12k of the connector 12C to a gate control unit (not shown in detail) employed in the main body of the electronic endoscope apparatus 2.

In the seventh electronic scope 10H, to protect the CCD 3 and repeater circuit 5 against an overvoltage, the normal-close type semiconductor switch SWc is turned OFF (namely, close circuit) whereby the signal/power source lines to these circuits 3 and 5 are brought into the same potential.

Figure 14A:
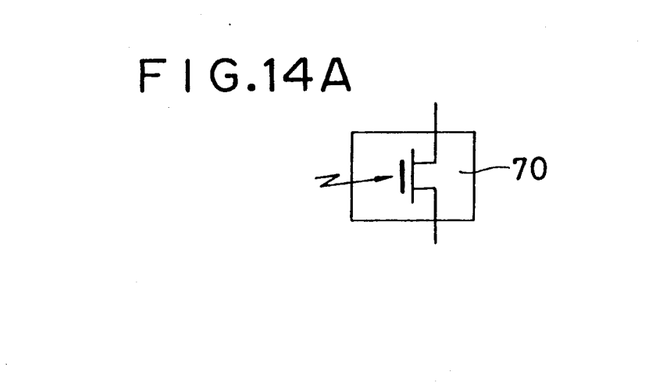
Figure 14B:
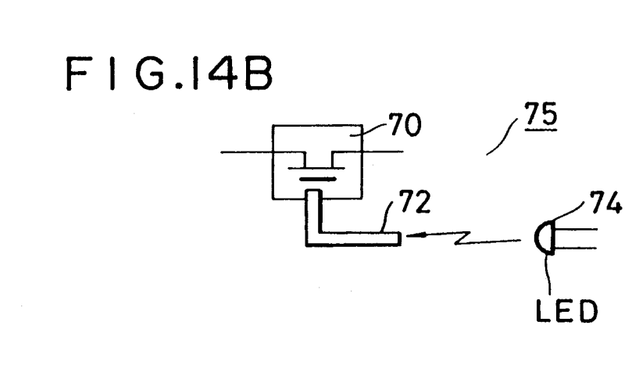

As modifications of this seventh embodiment, either an optical MOSFET (MOS type field-effect transistor) 70 as shown in FIG. 14A, or a photocoupler 75 constructed of the optical MOSFET 70, an optical fiber 72 and a light emitting diode (LED) 74 may be used as those semiconductor switches Swc, $SW_{0-1}$, $SW_{0-2}$ of FIG. 13.

In accordance with the above-described seventh preferred embodiment and the modifications thereof, the switching speeds can be improved as compared with those of the relay type overvoltage protecting circuits. Moreover, the noise margin of the seventh preferred embodiment and the modifications thereof can be furthermore improved.

Modifications

As apparent from the foregoing descriptions, the present invention is not limited to the above-described preferred embodiments, but may be modified, changed, and substituted without departing from the technical scope and spirit of the invention.

Figure 15A:
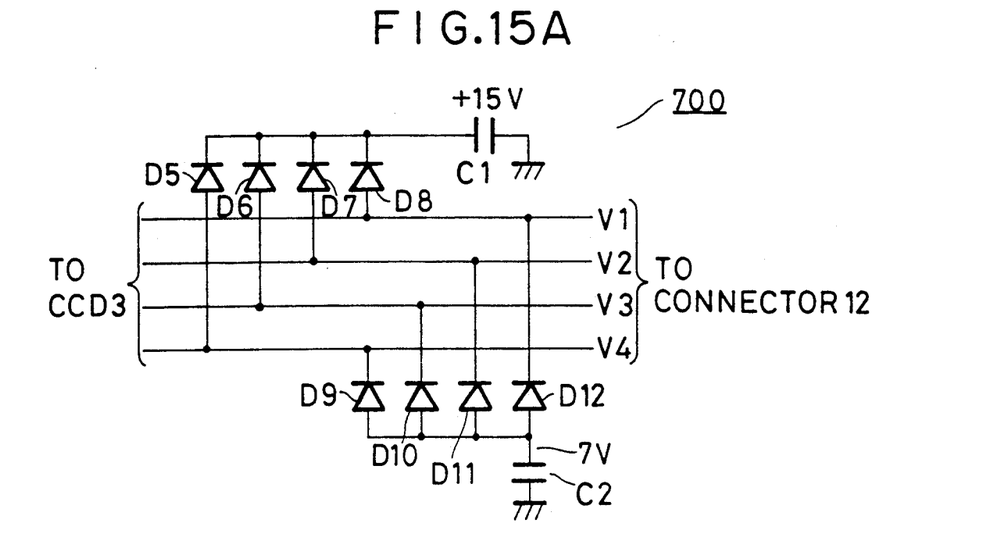
Figure 15B:
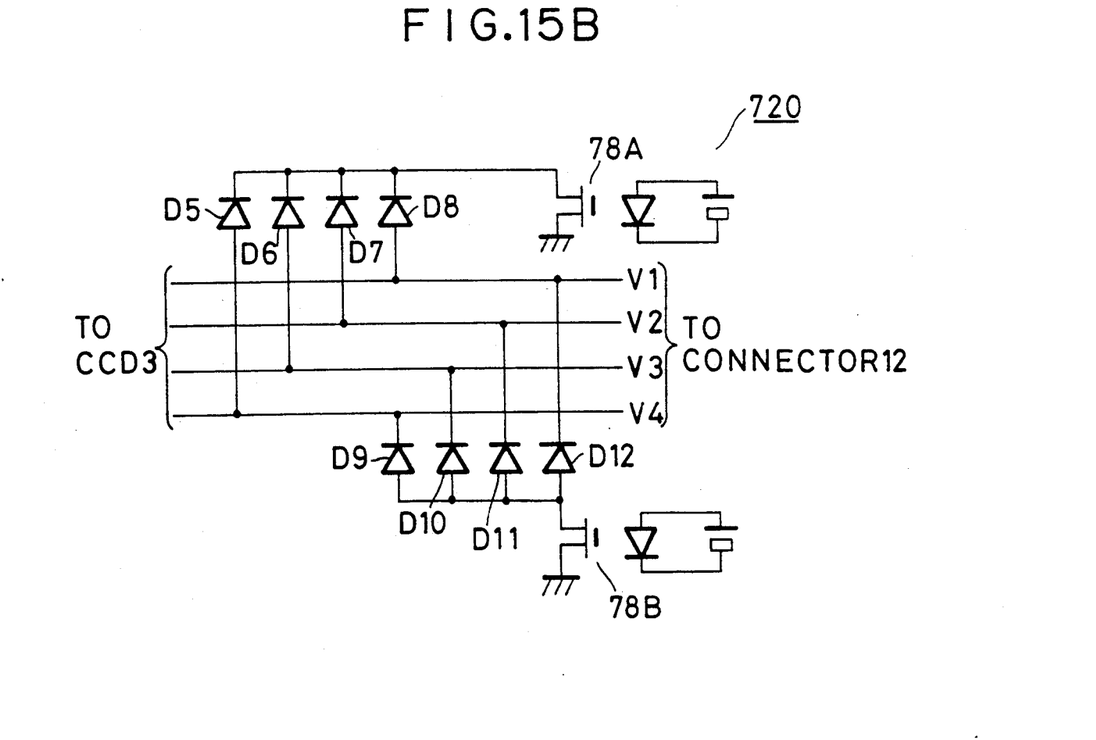
Figure 15C:
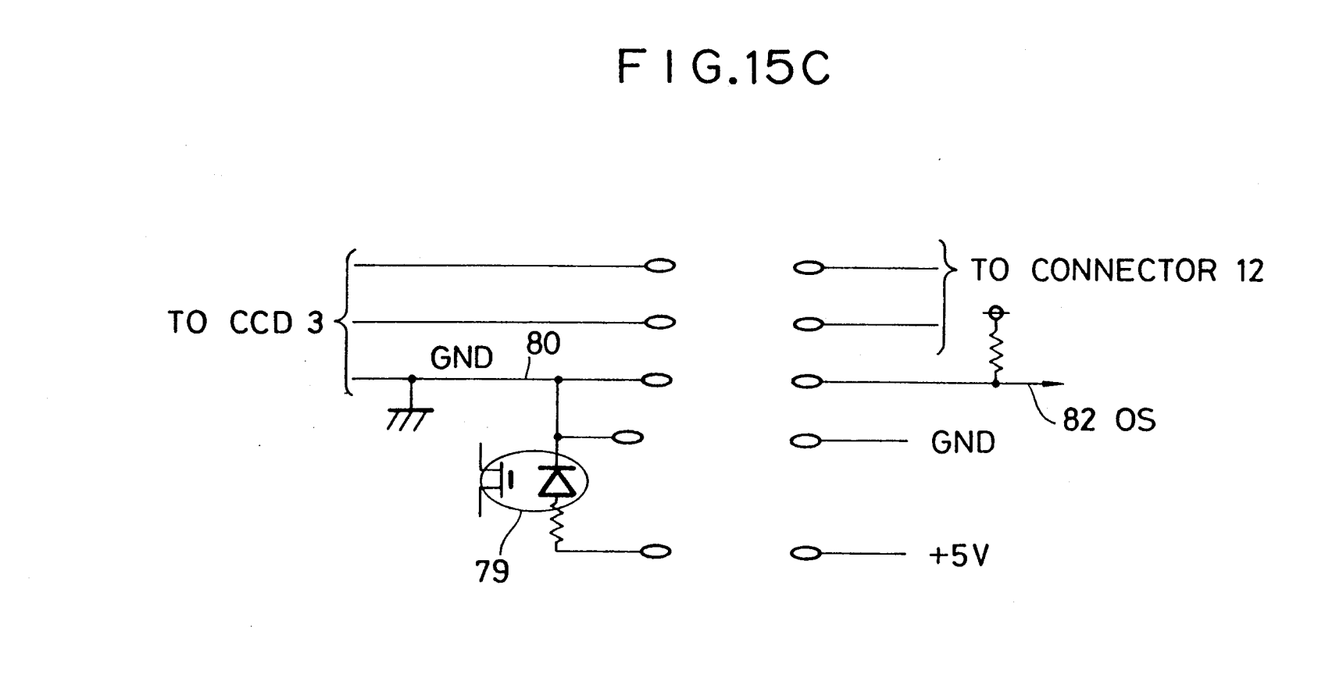

For instance, the third overvoltage protecting circuit 340 shown in FIG. 7 may be substituted by overvoltage protecting circuits 700, 720, 730 as shown in FIGS. 15A, 15B and 15C respectively. These overvoltage protecting circuits 700, 720 730 are suitable for the 3-level digital signal (e.g., +15 V, 0 V, −7 V). In the first modified overvoltage protecting circuit 700 shown in FIG. 15A, a voltage across a capacitor C1 becomes +15 V, whereas a voltage across a capacitor C2 becomes −7 V, while all of diodes D5 to D12 are conductive. The typical capacitance values of these capacitors C1 and C2 are 0.1 to 1 μF.

In the second modified overvoltage protecting circuit 720 shown in FIG. 15B, two sets of photocouplers 78A and 78B are employed in combination with the diode groups D5 to D8 and D9 to D12, so that these diode groups D5 to D8 and D9 to D12 are selectively brought into a conductive state or a non-conductive state by switching the photocouplers 78A and 78B.

Figure 16:
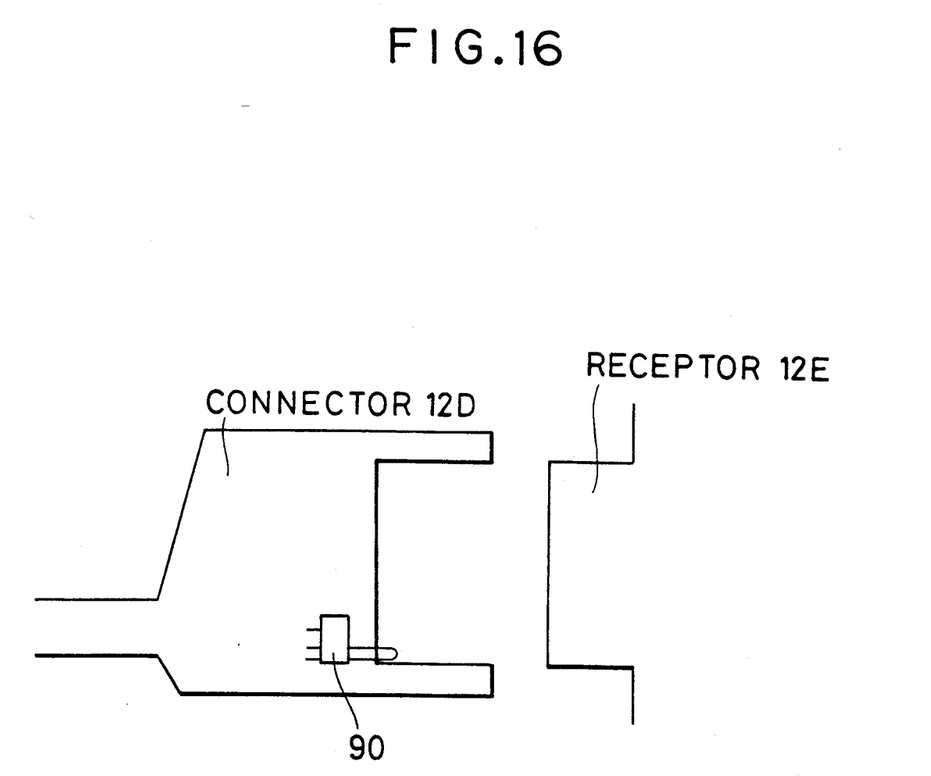

In the third modified overvoltage protecting circuit 730 shown in FIG. 15C, a photocoupler 79 is inserted to a ground line 80. When the photocoupler 79 is turned ON, the operating signal of CCD 3 appears on a signal line 82. Further, as shown in FIG. 16, a microswitch 90 is mounted inside a connector 12D. When the connector 12D is mechanically and electrically connected with a receptor 12E employed in the main body of the electronic endoscope apparatus 2, the microswitch 90 is mechanically depressed and actuated by the top surface of the receptor 12E. After this microswitch 90 is completely operated, the source voltage Vcc is applied form the main body to the CCD 3 and repeater circuit 5, whereby the overvoltage protection can be surely achieved.

What is claimed is:

1. An electronic scope used for an electronic endoscope apparatus, comprising:
   a solid-state image sensor for producing an image signal of a biological body under medical examination, said image signal being derived from a signal line of the image sensor; and,
   overvoltage protecting means for protecting said image sensor against an overvoltage caused by at least one of electrostatic energy induced on the electronic scope and interruption of source power supplied from the electronic endoscope apparatus to the image sensor, by maintaining at least said signal line at the same potential.

2. An electronic scope as claimed in claim 1, wherein said image sensor is a charge-coupled device.

3. An electronic scope as claimed in claim 1, wherein said overvoltage protecting means protects said image sensor against the overvoltage by connecting said sensor to a ground.

4. An electronic scope as claimed in claim 1, wherein said overvoltage protecting means is constructed of a relay having a plurality of relay contacts and a plurality of contact blades and operable in such a manner that when the electronic scope is disconnected from the electronic endoscope apparatus, said relay is deenergized and the signal line of the image sensor is maintained via said relay contacts and said contact blades at the same potential.

5. An electronic scope as claimed in claim 1, wherein said overvoltage protecting means is constructed of a plurality of diodes and a plurality of zener diodes connected in such a way that even when said overvoltage is produced, only a voltage smaller that said overvoltage, appearing across said diodes is applied to said image sensor, and also said zener diodes prevent currents flowing through the signal line to a ground line.

6. An electronic scope as claimed in claim 1, wherein said overvoltage protecting means is constructed of a relay having one set of relay contacts and contact blade, and also two diodes connected in such a manner that when the electronic scope is disconnected from the electronic endoscope apparatus, the signal line of the image sensor is connected via the relay contact and contact blade to a ground line by turning OFF the relay, and only a potential across one conducted diode is applied to the image sensor.

7. An electronic scope as claimed in claim 6, wherein said electronic scope further comprises a connector having a plurality of first connector pins connected to the image sensor, and also a plurality of second connector pins longer than said first connector pins, whereby when the connector of said electronic scope is connected to the electronic endoscope apparatus, the relay is energized via said second connector pins before said image sensor is driven via said first connector pins.

8. An electronic scope as claimed in claim 1, wherein said overvoltage protecting means includes a relay having a relay coil and a plurality of relay contacts and contact blades; and,
   said electronic scope further comprises a connector having a plurality of first connector pins connected via said relevant relay contacts and contact blades to said image sensor, and also a plurality of second connector pins connected to the relay coil in such a manner that when the connector 12B of the electronic scope is connected to the electronic endoscope apparatus, the image sensor is connected via the signal line and said first connector pins to the electronic endoscope apparatus before the relay is energized via said second connector pins by the electronic endoscope apparatus.

9. An electronic scope as claimed in claim 8, wherein said overvoltage protecting means further comprises:
   a switch for turning ON/OFF power supplied to the relay coil; and,
   a lever having a projection by which said switch is turned ON/OFF, while pivoting said lever.

10. An electronic scope as claimed in claim 6, wherein said overvoltage protecting means is constructed of a normal-close type semiconductor switch and two normal-open type semiconductor switches connected in such a manner that when said electronic scope is disconnected from the electronic endoscope apparatus, the normal-close type semiconductor switch shortcircuits said signal lines to said image sensor, whereby no overvoltage is applied to said image sensor.

11. An electronic scope as claimed in claim 10, wherein said semiconductor switches are optical MOSFETs (MOS type field-effect transistors).

12. An electronic scope as claimed in claim 10, wherein said semiconductor switches are photocouplers.

13. An electronic scope as claimed in claim 6, wherein said overvoltage protecting means includes:
   a first series circuit of a first diode group and a first capacitor connected between the signal lines and a ground line; and,
   a second series circuit of a second diode group and a second capacitor connected between the signal lines and the ground line.

14. An electronic scope as claimed in claim 6, wherein said overvoltage protecting means includes:
   a first series circuit of a first diode group and a first photocoupler connected between the signal lines and a ground line; and,
   a second series circuit of a second diode group and a second photocoupler connected between the signal lines and the ground line in such a way that said first and second diode groups are brought into a conductive state and a non-conductive state by switching ON/OFF said first and second photocouplers.

15. An electronic scope as claimed in claim 1, wherein said overvoltage protecting means is constructed of a photocoupler connected between a ground line and a power source in such a manner that said photocoupler is turned ON by said power source, said image signal of the image sensor appears on said signal line.

16. An electronic scope as claimed in claim 1, wherein a microswitch is mounted on an inside of a connector in such a manner that when the connector is connected to a receptor employed in the electronic endoscope apparatus, said microswitch is actuated to energize said really, before power is supplied to the image sensor.

* * * * *